United States Patent [19]

Lester

[11] 4,121,574

[45] Oct. 24, 1978

[54] METHOD AND APPARATUS FOR MEASURING AND RECORDING VITAL SIGNS OF A PATIENT

[75] Inventor: Robert W. Lester, Manhasset, N.Y.

[73] Assignee: Medicgraph Systems, Inc., New York, N.Y.

[21] Appl. No.: 786,706

[22] Filed: Apr. 11, 1977

[51] Int. Cl.$^2$ .............................................. A61B 5/00
[52] U.S. Cl. ............................. 128/2.05 R; 128/2 H
[58] Field of Search ............... 128/2.05 P, 2 R, 2.1 A, 128/2.05 R, 2.05 Q; 235/61.11 D, 61.11 E, 61.11 F, 61.12 M, 61.12 N; 340/146.3 C, 146.3 F, 146.3 G, 146.3 P, 146.3 Q, 146.3 Z, 146.3 WD; 73/362 AR; 40/310, 2.2, 21 C; 283/7; 346/335 ME, 162-164

[56] References Cited

U.S. PATENT DOCUMENTS

| | | | |
|---|---|---|---|
| 3,293,650 | 12/1966 | Buros | 235/61.11 D |
| 3,523,522 | 8/1970 | Whitehead | 128/2 R |
| 3,553,714 | 1/1971 | Birken | 346/163 |
| 3,656,473 | 3/1972 | Sodickson et al. | 235/61.12 N X |
| 3,660,916 | 5/1972 | McDermott et al. | 235/61.12 N X |
| 3,715,570 | 2/1973 | Weichselbaum et al. | 235/61.12 M |
| 3,732,573 | 5/1973 | Merka et al. | 346/162 X |
| 3,831,006 | 8/1974 | Chaffin et al. | 40/324 X |
| 3,871,362 | 3/1975 | Dunegan | 73/362 AR |
| 3,916,154 | 10/1975 | Hare et al. | 235/61.11 E |
| 3,940,742 | 2/1976 | Hudspeth et al. | 128/2 R X |
| 4,041,279 | 8/1977 | Foote | 235/61.11 E X |
| 4,051,522 | 9/1977 | Healy et al. | 128/2.1 A X |

FOREIGN PATENT DOCUMENTS 625,865 7/1949 United Kingdom ..................... 346/165

OTHER PUBLICATIONS

Roach, C. J., "Patient Data Processing — The Key to Hosp. Autom.", Amer. Jrnl. Med. Electr., Jan. - Mar., 1962, pp. 51-57.

*Primary Examiner*—William E. Kamm
*Assistant Examiner*—Francis J. Jaworski
*Attorney, Agent, or Firm*—Allison C. Collard; Thomas M. Galgano

[57] ABSTRACT

A method and apparatus for measuring and displaying the vital signs of a patient wearing an alpha-numeric identification bracelet, including a temperature sensing probe for making body contact with the patient, a portable, data-gathering acquisition unit and electronic anticipation circuitry disposed in the acquisition unit and coupled to the probe for sensing the change in patient temperature and predicting the stabilized temperature of the patient. There is a digital read-out coupled to the anticipated circuitry for indicating the predicted stabilized temperature of the patient, and an alpha-numeric sensor coupled to the acquisition unit and responsive to the alpha-numeric code for reading the code to identify the patient. The system also has a data storage memory coupled to the digital read-out and the anticipation circuitry for storing the predicted stabilized temperature and the indentification of the patient. The system further includes a pulse sensor disposed in the acquisition unit for detecting the pulse rate of the patient. The pulse sensor is coupled to the digital read-out and the data memory for storing the patient's pulse rate. A console is provided having a visual display, a digital keyboard for selecting identification concerning the patient, and a means for electronically producing patient vital-sign data on the visual display of said console in response to the keyboard. The console is coupled to the acquisition unit.

15 Claims, 13 Drawing Figures

METHOD AND APPARATUS FOR MEASURING AND RECORDING VITAL SIGNS OF A PATIENT

This invention relates to an improved combination electronic thermometer, pulse rate indicator and patient identification system.

More specifically, this invention relates to an electronic thermometer, and pulse rate indicator which is capable of recording the temperature of a patient and automatically identifying the patient from a code given to each patient.

It is common practice to measure the temperature of a patient by means of a glass bulb thermometer, incorporating a heat-responsive mercury column, which expands adjacent to a calibrated temperature scale. The glass thermometer is inserted into the patient, either orally or rectally, and subsequently removed after the temperature of the thermometer has stabilized at the body temperature of the patient. The time interval is usually in the order of 2-4 minutes. While this is not an objectionable time for a home use of a thermometer, it can be considered very slow where a nurse is required to measure the temperature of a multitude of patients, two or three times a day in a particular hospital area. Moreover, the mercury thermometer has a number of drawbacks, including the possibility of its breakage, the fact that the thermometer has to be shaken down before it can be reused, as well as sterilized, and the possibility of the patient becoming contaminated with the mercury, if the glass bulb shatters. The glass bulb thermometers are also very difficult to read and hence, measurements are prone to human error, particularly when made under poor lighting conditions.

During the early part of 1970, attempts to overcome the disadvantages of mercury glass bulb thermometers, have resulted in the development of several types of electronic thermometers, such as those disclosed in U.S. Pat. Nos. 3,702,076; 3,942,123; 3,940,742. In these systems, an electronic temperature probe, containing a thermister, is inserted into the patient's mouth, while the nurse carries an electronic system containing a digital temperature read-out. As the probe heats up to the patient's body temperature, the circuitry measures the rate of climb and the levelling off of the patient's temperature, and can make a predicted read-out of the patient's actual temperature. These devices use anticipation circuitry, so as to provide an advance indication of the anticipated temperature, which the thermister will finally stabilize. The nurse then manually records the indicated temperature of the patient on a chart or clipboard adjacent the patient's name, before proceeding to the next patient. There is no means provided for storing the data of the temperature or automatically identifying the name of the patient in these types of systems. Thus, the data which is recorded by the nurse, can be subject to notational errors, as each of the temperatures are taken. Moreover, the identity of the patient can be mistaken on the chart, and there is a possibility that certain patients will be omitted during the process of taking the temperatures.

Accordingly, the present invention provides for an electronic thermometer, pulse rate indicator and patient identification system, which is capable not only of reading the patient's temperature and pulse rate, but also identifying the patient from the wrist-band typically worn by all patients in hospitals, and automatically recording the temperature and pulse rate for a later read-out and analysis. The basic invention utilizes a thermister-type temperature sensing probe, which is coupled to a digital temperature-reading display that is carried by the nurse from patient to patient. The electronic circuitry employs temperature anticipation circuitry, so that the patient's temperature can be read within a few seconds, based upon the increase in temperature and its anticipated stabilized level. The other end of the temperature sensing probe includes a character-reader, such as a Universal Products Code (UPC) reader, that can identify the patient from a UPC symbol, consisting of vertical bars and spaces, which is placed on the patient's wristband. The probe may also utilize magnetic character reading, or MICR character-reading devices, such as those used on identifying checks in banks, in order to identify the patient from the characters on the wristband. The nurse scans the patient's wristband to identify the name of the patient. Then the patient's temperature is read, and this information, together with the temperature, is automatically stored in a memory system in the electronic circuitry of the digital read-out. The unit will not turn on the digital display if the nurse forgets to scan the patient first. The patient's pulse rate can be taken by a tissue-sensing detector. The unit then beeps to notify that data has been entered and the digital read-out is set for the next reading. For the purposes of keeping patients from contaminating each other during temperature readings, a plastic sleeve is generally inserted over the probe before it is given to each patient. The sleeve is removed and disposed of between each temperature reading, and a further sensor can be employed in the probe, to prevent the apparatus from being reset until the sleeve is removed and a new sleeve is inserted. After the nurse has taken a multitude of patient temperatures and pulse readings and their identity, the readings are stored in the memory of the portable read-out system. The system is then plugged into a small computer at the nurses' station, for recharging and reading out its memory onto a graph display or printer, so that a permanent record of each of the patients' temperatures can be established. The system can also be plugged into a central hospital computer input located at the patient's bed to record the temperature and patient identification data. The system can also be used with remoted CRT displays, to show the patient's room number and name as a locating device only, minus temperature and pulse.

It is therefore an object according to the present invention, to provide an electronic pulse rate, temperature measuring and patient identification system, for use in hospitals and other institutions.

Other objects and features of the present invention will become apparent from the following detailed description, considered in connection with the accompanying drawings, which disclose the embodiment of the system. The drawings are designed for the purpose of illustration only, and not as a definition of the limits of the invention. In the drawings, wherein similar characters denote similar elements throughout the several views:

Figures 1, 2, 3A, 3B, 4, 5:
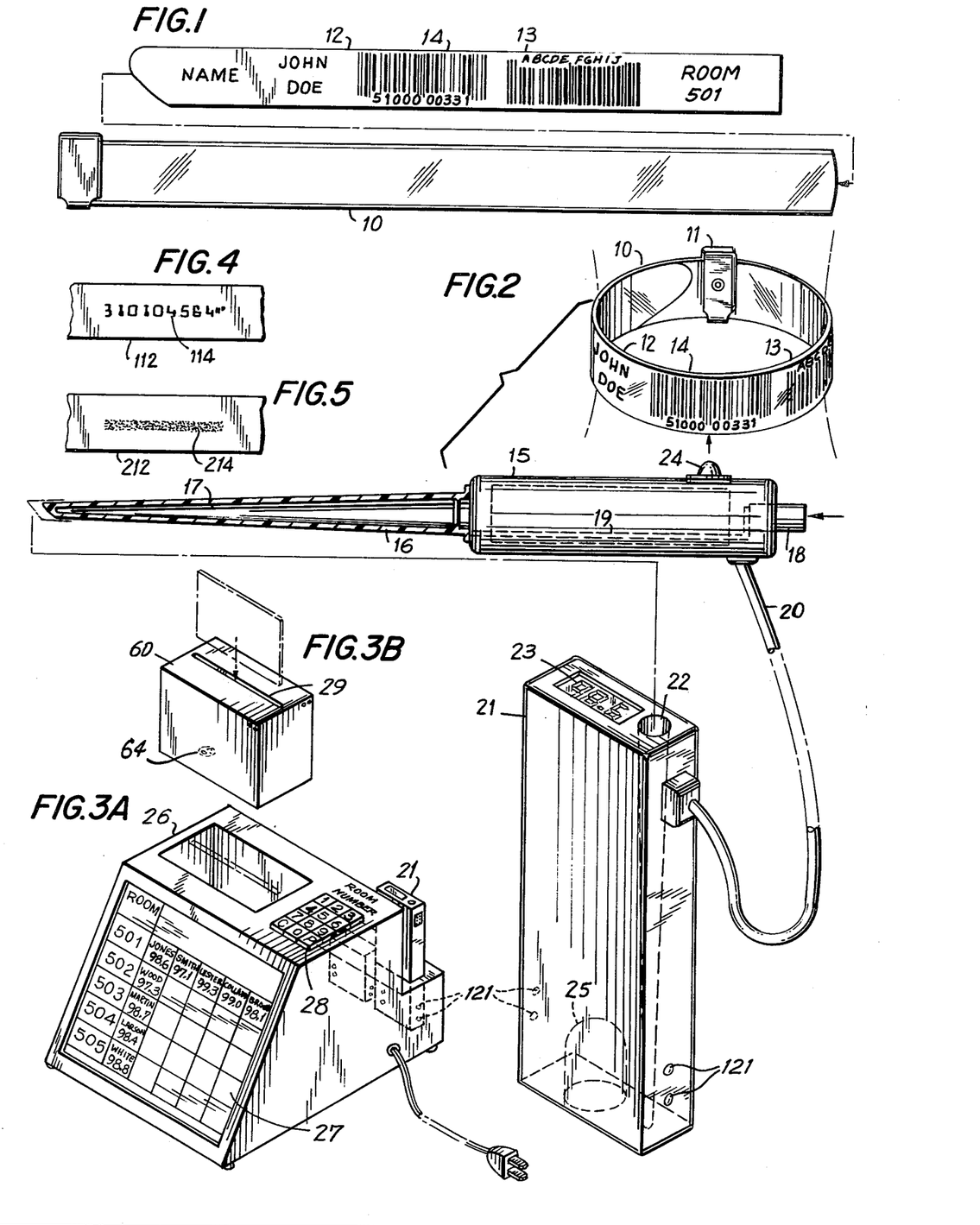
FIG. 1 is a plan view of an identification bracelet and its insert, typically used by hospitals.
FIG. 2 discloses an electronic temperature sensing probe and system, placed in close proximity to the wristband for identifying the patient.
FIG. 3A discloses a computer console for reading out and forming a graph of the collected temperature and patient information of the apparatus of FIG. 2.
FIG. 3B shows the removal of the solid state graph printer from the console.
FIG. 4 shows another type of code, which can be used on the patient's wristband.
FIG. 5 shows a magnetic type of code, which can be used on the wristband.

Referring to FIG. 1, there is shown a detailed view of a patient's identification bracelet 10, consisting of a plastic sleeve, which is open at one end and has a clamp or clasp 11, formed at the other end. Into this clear or translucent sleeve is inserted an identification slip 12, preferably made of paper or card, which contains a code, such as the Universal Products Code symbol 13, and 14, to identify the patient by number or name. The card may also include the patient's room number and other vital information, such as blood type, as may be customary in a hospital.

The code symbols 13 and 14 are modelled after the Universal Product Code that was adopted in 1973, and is a numbering system or alphanumeric display that assigns a unique number or name to every product or item currently in distribution. The code numbering system uses vertical bars and spaces, to form a scanable symbol, and optical font characters make up the corresponding human readable characters. The UPC symbol can be read by electronic scanning devices in either direction or upside down.

Symbols 13 and 14 may also be replaced by a magnetic ink code 114 printed on card 112 that can be read by an MICR unit, such as used by banks to read indicia off checks, as shown in FIG. 4.

FIG. 5 shows an alternative type of code, consisting of magnetic stripping 214 on card 212, which may contain patient identification data.

In FIG. 2, the wristband is closed by means of clasp 11 onto a patient's wrist and the patient's identification symbol 14 or name 13, 114 or 214 is displayed. FIG. 2 also shows a thermister type temperature sensing device having a handle 15 and a probe 17, which can be used orally or rectally. A plastic sterile sleeve 16 covers the thermister probe 17. This sleeve can be ejected after use by depressing button 18 at the rear of the probe. An L-shaped lever 19, in contact with the button, ejects the plastic sleeve from the probe after each temperature reading. The probe is connected by means of an electrical conductor 20 to an acquisition unit 21, which includes a digital read-out 23 on one surface. Along one side of handle 15 is an optical or magnetic scanner 24, which is capable of reading the identification data 14, 114 or 214, that is contained on the patient's wristband 10. Scanning device 24 will transmit via conductor 20 to the electronic circuit in unit 21, the magnetic code or optical characters that appear on symbols 13, 14, 114 or 214, and the memory circuit will translate that signal into an alphanumerical code which identifies the patient.

Acquisition unit 21 stores not only patient temperature and identification, but also pulse rate as well. For example, cylindrical aperture 25 formed in the bottom of acquisition unit 21 will allow the patient to insert his finger into the cavity so that his pulse rate can also be sensed electronically. In aperture 25 of the acquisition unit, there is included a source of light and a light sensor which responds to the light transmitted through the finger-tip and varies with the frequency related to the patient's pulse rate. The volume of blood in the patient's finger-tip changes the absorption of light from the source, causing the light impinging on the sensor to change as a function of the amount of blood in the patient's finger-tip which, in turn, varies with his pulse. The modulated light is fed into electronic sensing circuitry to produce a digital read-out on indicator 23 of the pulse rate. A pulse rate monitor using this system of peripheral pulse measurement is manufactured by Meditron Instrument Corporation in Milford, N.H., as its "Vital 1" unit.

FIG. 3 shows a CRT other type of display unit 26 having the CRT display 27 on its front-inclined surface, which shows the room number, name and temperature for each of the patients in that room. Unit 26 receives acquisition unit 21 in a compartment in the rear portion, so that the data can be electronically transferred from the acquisition unit via contacts 121 to the CRT display. On the top surface is provided a digital keyboard 28 and a slot 29 for receiving a data card printer 60 for imprinting the temperature, pulse and patient identification onto a permanent record card.

Figures 6, 7:
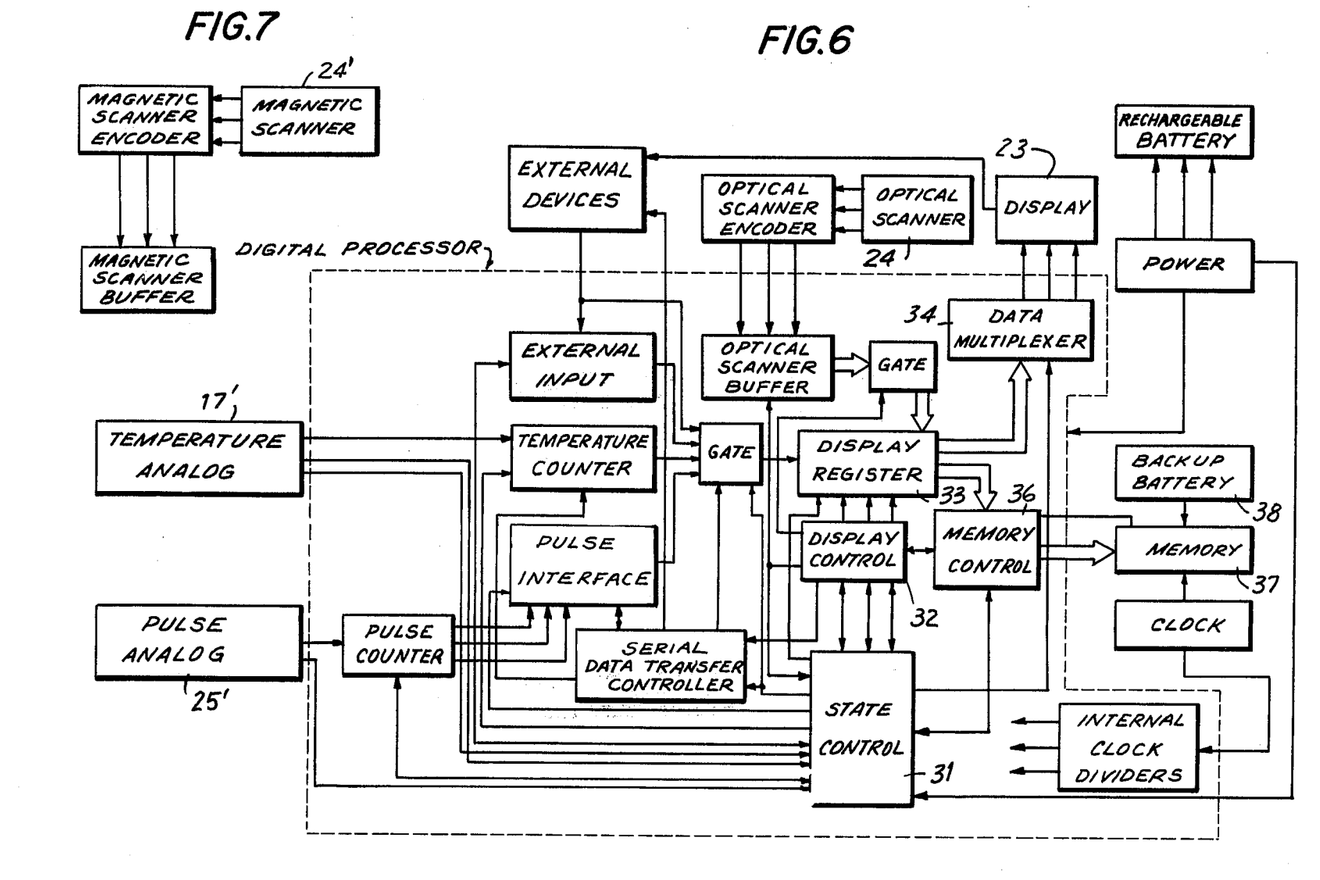
FIG. 6 is an electronic schematic diagram of the temperature measuring and patient identification system, using an optical scanner.
FIG. 7 shows a minor variation of the circuit diagram of FIG. 6, for use with a magnetic scanning device.

Referring to FIG. 6, there is shown an electrical block diagram of the circuitry of acquisition unit 21, which includes temperature analog circuit 17', respiration analog 30 and pulse analog circuit 25'. All these analog signals are converted to digital form within the circuit. There is a state controller 31, comprising a logic that advances the acquisition unit through various operational modes. Additionally, controller 31 determines if the probe portions are attached to the system. Controller 31 is also responsive from signals coming from scanner 24 and its analog circuits in order to initiate the operation of the unit. The incoming data from each of the analog circuits is transferred to the state controller and then to a display controller 32, and into display register 33. From display register 33, the data is then fed into a data multiplexer 34, where it is gated to digital display 23. Data in display register 33 also feeds a memory control circuit 36, where the data is stored in a read-write memory 37. A back-up battery 38 eliminates any possible memory loss in read-write memory 37, if there is a power failure in the system. This battery would not be necessary if a non-volitile memory is used.

The acquisition unit of the present invention can be made capable of storing approximately 100 readings in combination with the UPC code or a magnetic code.

FIG. 7 shows a variation of the circuit of FIG. 6, wherein optical scanner 24, its encoder and buffer are replaced with a magnetic scanner 24' and a magnetic encoder and buffer.

Figure 8:
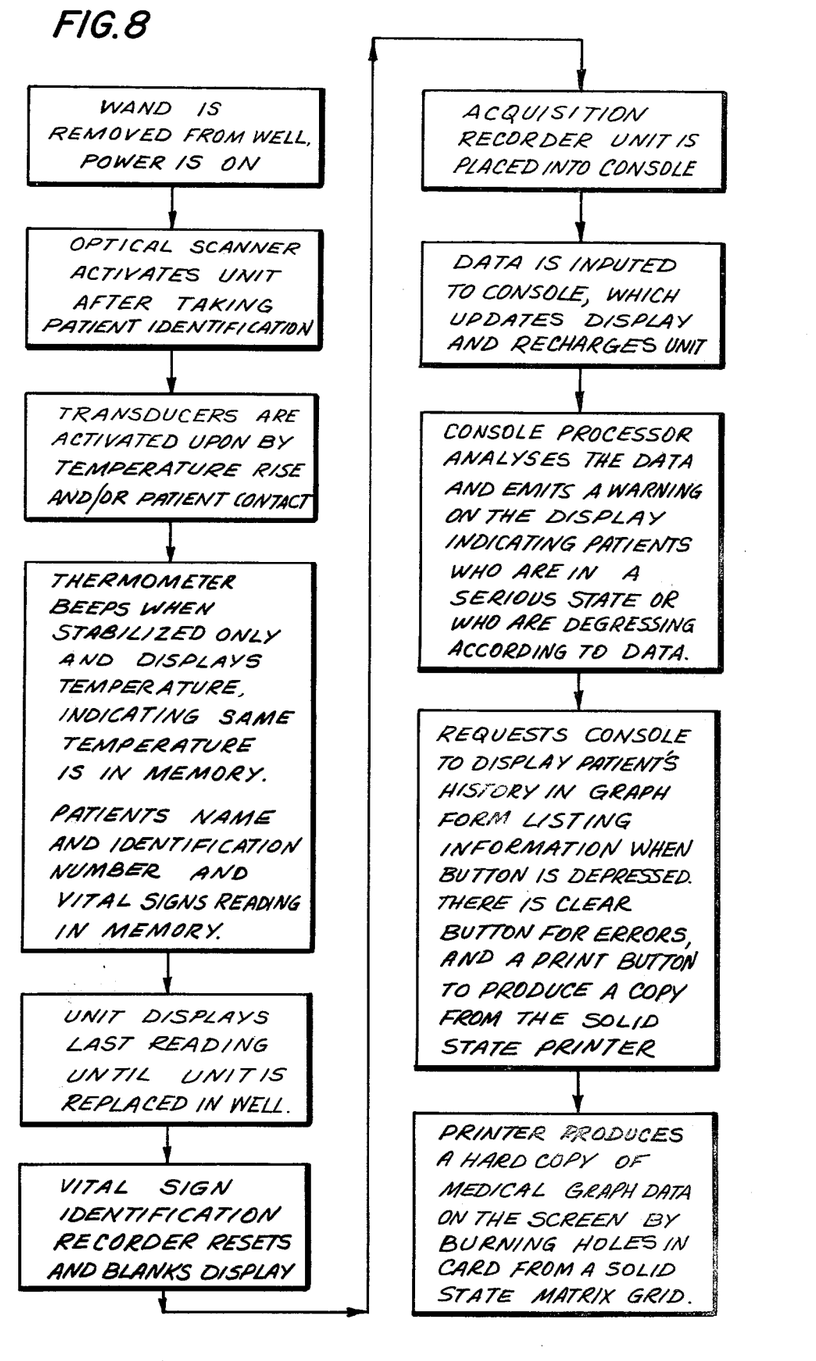
FIG. 8 is a flow chart, illustrating the method of measuring temperature and identifying patent data by the system, according to the invention.

FIG. 8 is a flow chart diagram, showing the use of the digital thermometer system and its sequence of operations. In FIG. 8, when temperature measuring probe 17 is removed from well 22 in acquisition unit 21, a switch disposed in the well turns the power on in unit 21. The nurse will then pass optical scanner 24, or an equivalent magnetic scanner 24', over the code printed on the patient's wirst-band. The code will identify the patient by name and number and activate the thermister for a temperature reading. The thermister located at the end of probe 17 is placed in contact with the patient and will then sense his temperature rise. The acquisition unit will produce an audible sound when the temperature approaches the stabilized temperature of the patient, as sensed by its anticipation circuitry. The temperature will then be displayed in digital read-out 23 and stored in memory circuit 37, along with the patient's name and identification number and other vital sign readings, such as the pulse measured by pulse analog 25' or the respiration rate. The temperature or pulse rate, whichever was the last reading taken of the patient, will continuously be displayed on read-out 23 until the probe is replaced back into well 22. Acquisition unit 21 will then reset itself and digital read-out 23 will become blank. Sterile plastic sleeve 16 will have to be removed after each temperature reading, before the probe will fit into aperture 22, to reset the unit. This assures that a new sterile sleeve will be inserted onto the probe before the next temperature reading is taken.

After a number of temperature readings have been taken, the acquisition unit is placed into a compartment at the rear of console 26, so that contacts 121 will engage similar contacts in the console unit. The data stored in memory circuit 37 is fed into the console, which will update and display the data on a CRT screen, as well as recharge the battery of the acquisition unit 21.

Console 26 will analyze the data and provide a warning on the display, if there is a change in the temperature reading, such as more than one degree F. Moreover, the light behind the patient's name will start to blink on the CRT display simultaneously with the alarm, so as to indicate patients who are in a serious state or who are digressing according to previously-recorded data.

The digital keyboard 28 on the top surface of console 26 allows the observer, such as a doctor, to press in the room number and observe the stored information concerning pulse rate and temperature on each of the patients in the room. There is also a clear button "C", such as if there is an error in the reading, and a print button "P", to produce a copy from the solid state printer 60, which is inserted into the top of the unit. Printer 60 will produce a hard copy of the medical graph data on the screen by burning holes in a card from a solid state matrix grid. A more detailed explanation of the printer is provided in this application, regarding FIGS. 10-12.

Figure 9:
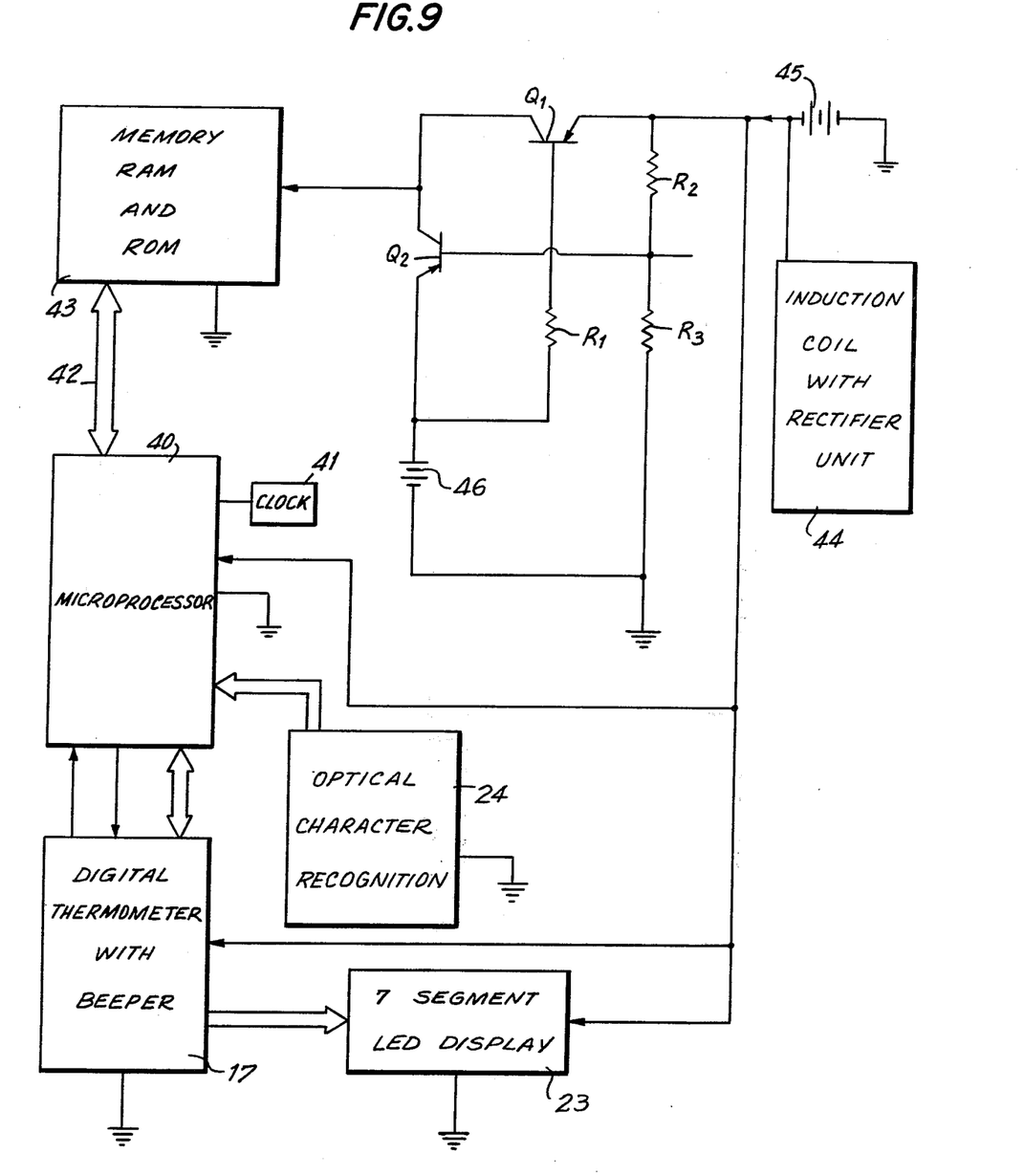
FIG. 9 is an electronic block diagram of another embodiment of the invention.

FIG. 9 is a circuit block diagram of another embodiment of an electrical circuit over that shown in FIGS. 6 and 7, which can be used for acquisition unit 21. The heart of the system is a microprocessor 40, which is a miniature computer capable of sequencing the operations shown in FIG. 8. A clock 41 drives microprocessor 40, and RAM or ROM memory 43 coupled through line 42, stores the patient's identification, temperature and pulse rate data, which is picked up by optical scanner circuit 24 and digital thermometer probe 17. The thermometer also feeds display 23, which is on the top surface of acquisition unit 21. An auxiliary battery circuit can be provided, having a battery 45 and an induction coil with a rectifier unit 44, which can be used to pick up power from an AC field when the acqusition unit is placed in the socket behind console unit 26. A rechargeable battery 46 is connected to the emitter of a second transistor of the charging circuit and will be charged up from the induction and rectifier unit 44 after each day's use of acquisition unit 21.

Figure 10:
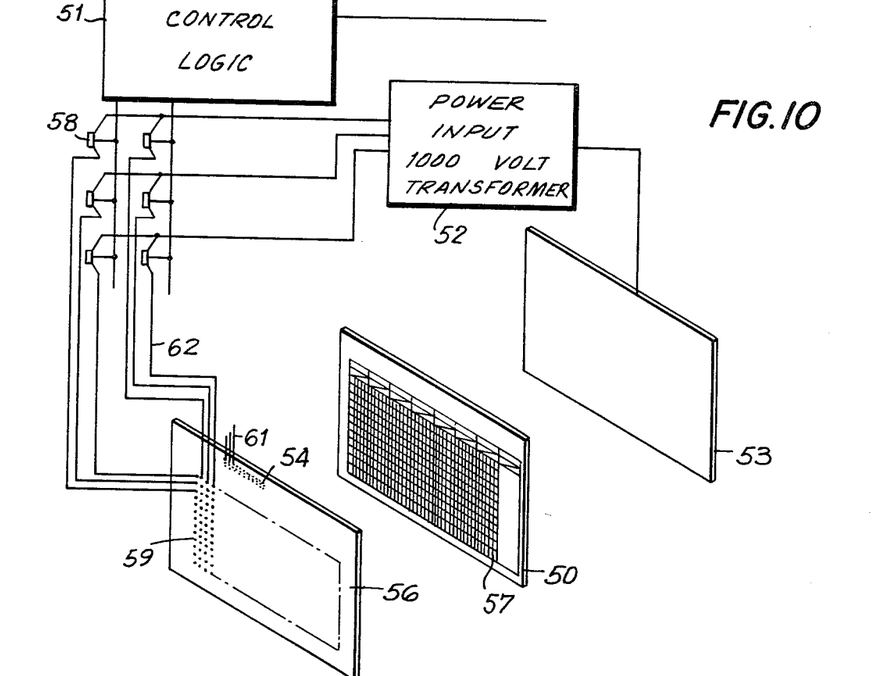
FIG. 10 is an electronic diagram, partly in schematic form, showing the operation of a solid state graph printer, used in combination with the patent measuring system.
Figure 11:
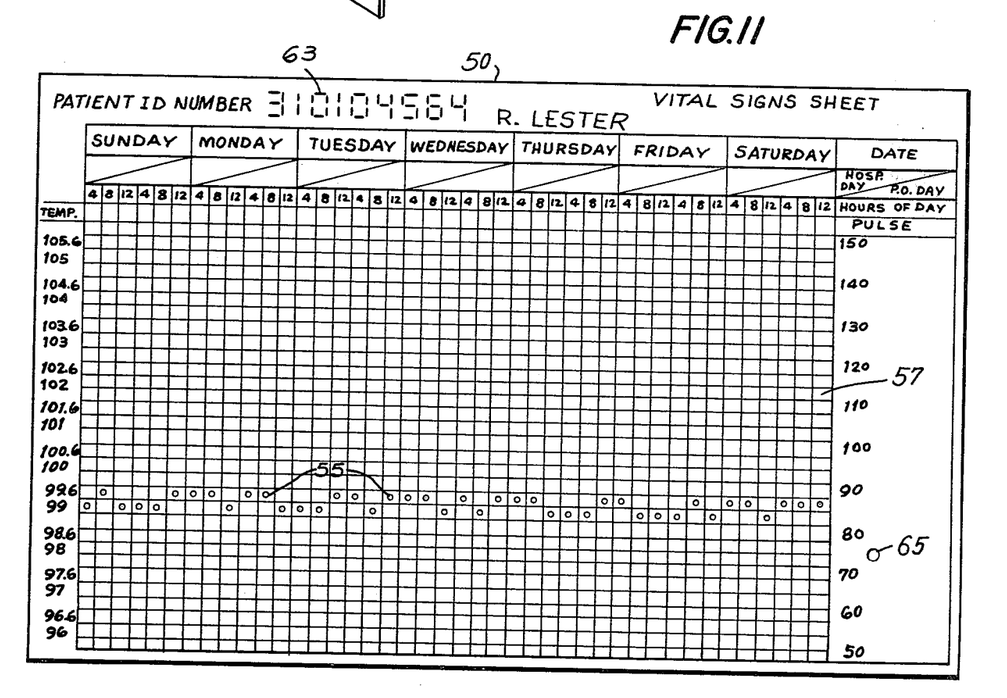
FIG. 11 is a detailed view of the temperature and pulse chart used in the graph system of FIG. 10.

FIGS. 10 and 11 show a detailed illustration, partly in schematic form, of the solid state printer 60 (FIG. 3b), which is inserted into the console unit of FIG. 3a. In FIG. 10, there is shown a patient's daily graph for indicating temperature and pulse rate reading, printed on a card 50, which is disposed between a high-voltage metallic plate 53 and a control grid plate 56. On plate 56, in conjunction with the printed portion of card 50 are disposed a plurality of metal contacts 59. These contacts are spaced in close proximity with respect to each other, so that there is a contact for each of the rectangular data entry spaces 57, on card 50. A control logic circuit 51, which is fed from the stored memory circuit in acquisition unit 21, controls a plurality of semi-conductor switches 58, which activate individual contacts 59 through conductors 62, to bring these particular contacts to ground potential, so that a large, potential difference will exist between the selected contact and plate 53. When plate 53 and grid card 56 are separated by only the width of card 50, the high potential between selected contacts 59 of grid 56 and plate 53, will burn selective holes 55 and 65 into the card. With the temperature being listed along the left-hand edge of the card and the days of the week in four-hour intervals being spaced along the top of the card, selective temperature readings can be displayed on the card, so that the entire week's record of the patient's temperature and pulse activity can be seen. In addition, grid plate 56 also includes a plurality of contacts 54 along its top edge and coupled to conductors 61, which are also fed to a control logic circuit in a manner similar to conductors 62, so that the patient's identification number and name 63, can also be burned into the top of the card at the same time temperature readings and pulse readings 55 and 65, are burned into the card. Printer 60, as seen in FIG. 38, includes a plug terminal 64 on its bottom surface, so as to interconnect with console 26. An extension cord having a similar plug terminal 64, could also be plugged into console 26 and connected to one or more printers at a remote location.

Figure 12:
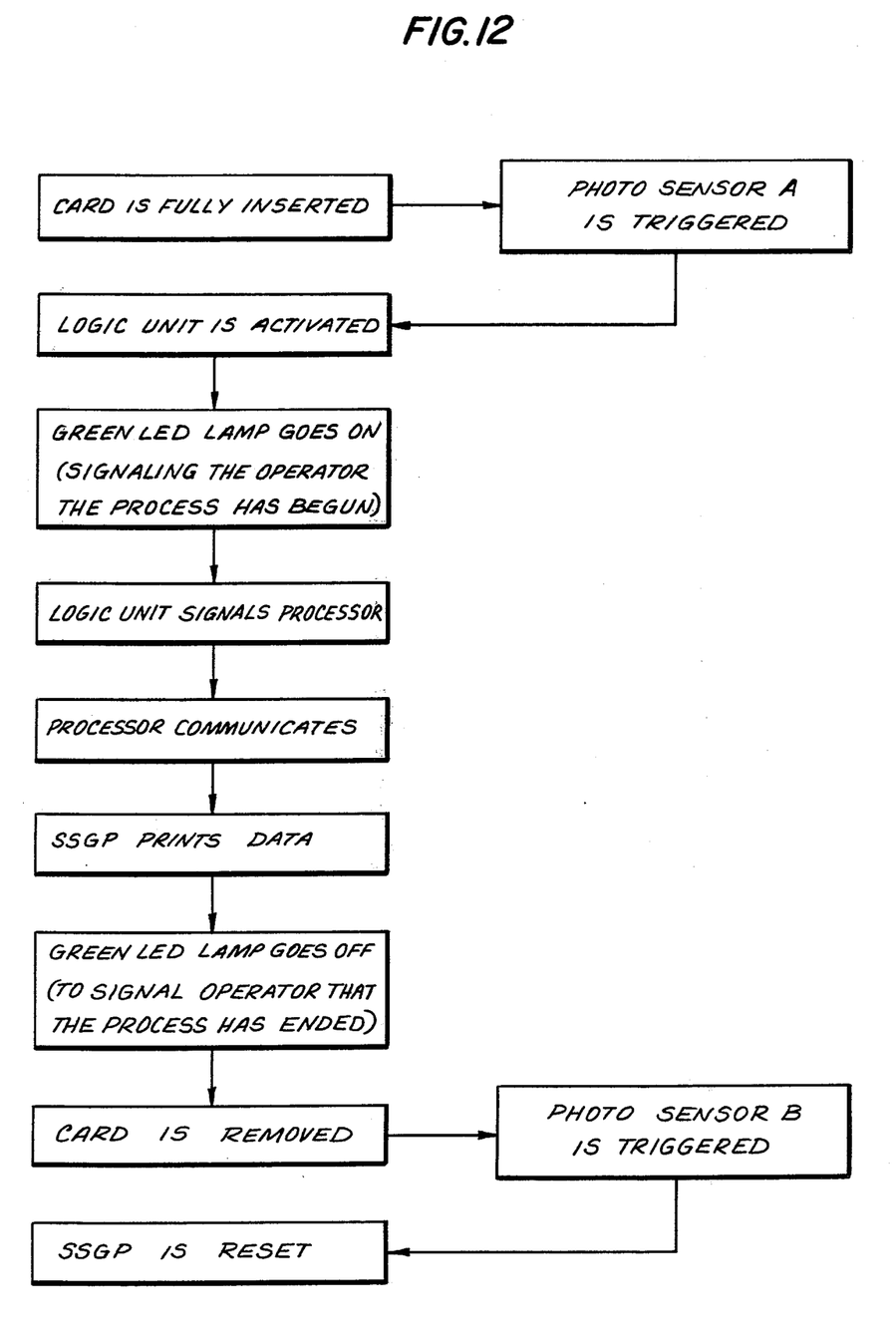
FIG. 12 is a flow chart, showing the operation of the solid state graph printer of FIG. 10.

FIG. 12 outlines the sequence of making a hard copy of patient's vital sign data. When card 50 is inserted into slot 29 of printer 60, a photosensor within the slot is triggered to activate control logic circuit 51. A lamp on console 26 will turn on, signalling the operator that the solid state printing process has begun. Logic unit 51 will signal, for example, the microprocessor 40 of FIG. 9, so that selective contacts 59 are energized to create a potential difference between themselves and high-voltage plate 53. When all of the data has been burned onto card 50, the lamp on console 26 will turn off, signalling the end of the process. The card can then be removed and the photosensor within slot 29, will reset the solid state graph printer 60.

Grid plate 56 containing the multitude of contacts 59, is preferably constructed of an insulating material and the contacts are preferably formed as rivets, flush to the surface of the grid and there is a few thousandths clearance to the surface of card 50, after it is inserted. Graph card 50 is preferably constructed of a thin, paper material that is sufficiently rigid, so that it will hold its dimensional stability when inserted into slot 29. Plate 53 is preferably a polished, metal plate, electrically connected to a high-voltage transformer 52, which is coupled to semi-conductor switches 58.

The entire vital measuring system, consisting of acquisition unit 21, console 26 and solid state printer 60, can be interconnected to a hospital central computer system via either outputs 121 of unit 21, or plug 64 of printer 60. It would then be possible for a nurse or doctor to use any CRT console display in the hospital to monitor select patients, once the patient's number is inserted by keyboard 28.

The UPC bar code can also be printed in multiple colors on the wrist-bands, in order to reduce the size of the bar code and increase the information that can be read by the optical scanner.

While only a few embodiments of the present invention have been shown and described, it will be obvious that many changes and modifications may be made thereunto without departing from the spirit and scope of the invention.

What is claimed is:

1. An apparatus for measuring and displaying the vital signs of a patient having an alpha-numeric identification device, comprising:
  a temperature sensing probe for making body contact with the patient, said temperature sensing probe comprising an elongated, cylindrical rod having a thermister sensing element for contact with the patient's body;
  a portable, data-gathering acquisition unit;
  electronic anticipation circuitry disposed in said acquisition unit and coupled to said probe for sensing the change in patient temperature and predicting the stabilized temperature of the patient;
  digital indication means coupled to said anticipation circuitry for indicating the predicted stabilized temperature of the patient;
  alpha-numeric sensing means mounted on said probe and coupled to said acquisition unit and responsive to a printed or magnetic code for reading said code to identify the patient;
  data storage means coupled to said digital indication means and said anticipation circuitry for storing the predicted stabilized temperature and the identification of the patient.

2. The apparatus as recited in claim 1 additionally comprising pulse sensing means disposed in said acquisition unit for detecting the pulse rate of the patient, said pulse and sensing means being coupled to said digital indication means and said data storage means for storing the patient's pulse rate.

3. The apparatus as recited in claim 2, wherein said pulse sensing means comprises a cavity formed in said acquisition unit for receiving the patient's finger, a light source for illuminating the expansion and contraction of the patient's blood vessels, and an optical detector for measuring the change in frequency of the light responsive to the blood vessel movement, and an analog to digital converter for converting the blood vessel movement into electrical pulse signals, and a counter coupled to said converter for determining the pulse rate.

4. The apparatus as recited in claim 1 additionally comprising a console having a visual display means for coupling said acquisition unit to said console, a digital keyboard mounted on said console for selecting identification concerning the patient and means for electronically producing patient vital-sign data on the visual display of said console in response to said keyboard.

5. The apparatus as recited in claim 4, wherein said console additionally comprises solid state printing means coupled to said console, said printing means having a slot for receiving a card for printing the vital-sign data gathered by said acquisition unit and stored in said data storage means.

6. The apparatus as recited in claim 5, wherein said solid state printing means comprises a gride plate having a multitude of spaced-apart contacts to form rows and columns on said plate;
  control logic means having its input coupled to said data-storage means, and having a multitude of outputs, each connected to one of said grid plate contacts; and
  a high-voltage plate disposed adjacent to said gride plate opposite said contacts, said voltage plate being connected to a high-voltage power source responsive to said control logic means, so that when a card is disposed between said two plates, the activation of selective contacts will create a large potential difference between the selected contacts and said voltage plate, to burn selective holes in said card, responsive to the vital signs of the patient.

7. The apparatus as recited in claim 6, wherein said grid plate includes contacts disposed in an alphanumeric pattern for imprinting the patient's number and name on the card, in response to said data storage means.

8. The apparatus as recited in claim 7, wherein the data card comprises a plurality of rows and columns defining boxes, each in registry with a contact of said printer, said columns defining the time of reading of the vital sign, and said rows defining the magnitude of the vital sign.

9. The apparatus as recited in claim 4, wherein said means for coupling said acquisition unit to said console comprises a recessed compartment disposed in said console, for receiving said acquisition unit, said compartment including a plurality of contacts for engagement with similar contacts in said acquisition unit, so that the vital-sign information stored in said data-storage means can be transferred to the visual display of said console.

10. The apparatus as recited in claim 1, wherein the alpha-numeric identification device comprises a bracelet for securement to the wrists of the patient and including an alpha-numeric code for identifying the patient.

11. The apparatus as recited in claim 10, wherein the alpha-numeric code comprises the Universal Product Code, and said scanning means comprises an optical product code scanner.

12. The apparatus as recited in claim 10, wherein the alpha-numeric code comprises a magnetic strip disposed on said bracelet and said scanning means comprises a magnetic recording head.

13. The apparatus as recited in claim 10, wherein said alpha-numeric code comprises computer characters and said scanning means comprises a MICR reader.

14. The apparatus as recited in claim 1, wherein said electronic anticipation circuitry comprises a microprocessor, said data storage means comprises a RAM and ROM memory coupled to said microprocessor, said temperature sensing probe comprises a digital thermometer and said digital indication means comprises a multiple segment, solid state digital display.

15. The apparatus as recited in claim 1, wherein said acquisition unit comprises a probe-receiving cavity having a diameter slightly larger than said probe rod, and means disposed in said cavity and responsive to said probe for resetting said anticipation circuitry.

* * * * *